(12) United States Patent
Säll (10) Patent No.: US 12,156,965 B2
(45) Date of Patent: Dec. 3, 2024

(54) ARRANGEMENT FOR AEROSOL DISPENSER, AEROSOL DISPENSER AND METHOD

(71) Applicant: SHL MEDICAL AG, Zug (CH)

(72) Inventor: Daniel Säll, Segeltorp (SE)

(73) Assignee: SHL Medical AG, Zug (CH)

( * ) Notice: Subject to any disclaimer, the term of this patent is extended or adjusted under 35 U.S.C. 154(b) by 939 days.

(21) Appl. No.: 17/275,112

(22) PCT Filed: Sep. 12, 2019

(86) PCT No.: PCT/EP2019/074310
§ 371 (c)(1),
(2) Date: Mar. 10, 2021

(87) PCT Pub. No.: WO2020/064340
PCT Pub. Date: Apr. 2, 2020

(65) Prior Publication Data
US 2022/0047824 A1 Feb. 17, 2022

(30) Foreign Application Priority Data
Sep. 27, 2018 (EP) ..................................... 18197285

(51) Int. Cl.
*A61M 15/00* (2006.01)
*A61M 11/00* (2006.01)
(Continued)

(52) U.S. Cl.
CPC ...... *A61M 15/0001* (2014.02); *A61M 11/007* (2014.02); *A61M 15/0036* (2014.02);
(Continued)

(58) Field of Classification Search
CPC .. A61M 11/00; A61M 11/006; A61M 11/007; A61M 15/00; A61M 15/0001;
(Continued)

(56) References Cited

U.S. PATENT DOCUMENTS 5,964,416 A 10/1999 Jaeger et al.
6,209,738 B1 4/2001 Jansen et al.
(Continued)

FOREIGN PATENT DOCUMENTS

JP 2001-161792 A 6/2001
JP 2013-529972 A 7/2013
(Continued)

OTHER PUBLICATIONS

International Search Report and Written Opinion for Int. App. No. PCT/EP2019/074310, mailed Nov. 26, 2019.

*Primary Examiner* — Colin W Stuart
(74) *Attorney, Agent, or Firm* — McDonnell Boehnen Hulbert & Berghoff LLP (57) ABSTRACT

An arrangement for activating an aerosol dispenser having a conveying tube for conveying a liquid; a movable holding member holding the conveying tube; a rotatable base; and a container chamber between the holding member and the base, wherein the arrangement is configured to transmit a loading rotation of the base to a substantially axial loading movement of the holding member towards the base, and wherein the holding member has a locking structure exposed to the container chamber. An aerosol dispenser having the arrangement and a method for activating an aerosol dispenser are also provided.

14 Claims, 5 Drawing Sheets

(51) Int. Cl.
  *G01F 11/00*    (2006.01)
  *G01F 11/02*    (2006.01)
(52) U.S. Cl.
  CPC ....... *A61M 15/0086* (2013.01); *G01F 11/006* (2013.01); *G01F 11/025* (2013.01)
(58) Field of Classification Search
  CPC .......... A61M 15/0028; A61M 15/0088; A61M 15/0086; A61M 15/0036; A61M 15/0035; A61M 15/0033; A61M 2205/07; A61M 2205/071; A61M 2205/073
  See application file for complete search history.

(56) References Cited

U.S. PATENT DOCUMENTS

| | | | | |
|---|---|---|---|---|
| 6,988,496 | B1* | 1/2006 | Eicher | B05B 11/0044 128/200.14 |
| 2011/0251553 | A1 | 10/2011 | Ratjen et al. | |
| 2012/0090603 | A1 | 4/2012 | Dunne et al. | |
| 2012/0325204 | A1 | 12/2012 | Holakovsky et al. | |
| 2013/0056888 | A1* | 3/2013 | Holakovsky | G06M 1/241 261/78.2 |
| 2013/0125881 | A1* | 5/2013 | Holakovsky | G06M 1/026 128/200.21 |
| 2013/0206136 | A1* | 8/2013 | Herrmann | A61M 15/0028 128/200.21 |
| 2015/0040890 | A1* | 2/2015 | Besseler | A61M 15/0038 128/200.14 |
| 2016/0303330 | A1 | 10/2016 | Holmqvist | |

FOREIGN PATENT DOCUMENTS

| | | |
|---|---|---|
| JP | 2014-521369 A | 8/2014 |
| WO | 2009/047173 A2 | 4/2009 |
| WO | 2011/160932 A1 | 12/2011 |

* cited by examiner

ARRANGEMENT FOR AEROSOL DISPENSER, AEROSOL DISPENSER AND METHOD

CROSS REFERENCE TO RELATED APPLICATIONS

The present application is a U.S. National Phase Application pursuant to 35 U.S.C. § 371 of International Application No. PCT/EP2019/074310 filed Sep. 12, 2019, which claims priority to European Patent Application No. 18197285.2 filed Sep. 27, 2018. The entire disclosure contents of these applications are herewith incorporated by reference into the present application.

TECHNICAL FIELD

The present disclosure generally relates to an aerosol dispenser. In particular, an arrangement for activating an aerosol dispenser, an aerosol dispenser comprising the arrangement, and a method for activating an aerosol dispenser, are provided.

BACKGROUND

An aerosol dispenser is used to create an aerosol, i.e. a mist of liquid particles. Some aerosol dispensers use a gas to propel the liquid and some aerosol dispensers use mechanical solutions without a propelling gas to expel the liquid.

One type of aerosol dispenser comprises a base, a piston, a conveying tube, a spring, a dose chamber, a spray nozzle and a container, e.g. containing a drug. When the user rotates the base, e.g. 180°, the piston and the conveying tube are moved to compress the spring. As the conveying tube moves, the dose chamber is expanded and an underpressure is established therein. The underpressure causes the liquid in the container to be sucked into the dose chamber by the conveying tube. The user may then push a button to release the piston holding the conveying tube to expel a dose from the dose chamber through the spray nozzle as an aerosol.

U.S. Pat. No. 5,964,416 A discloses a miniaturized device for pressurizing fluid. The device includes a hollow piston that provides a fluid path and a valve member. The valve member is configured for axial movement so that the valve axis remains parallel to the piston axis. The valve member is arranged at one end of the hollow piston. The valve member may be partially or completely disposed within the hollow piston. The device is particularly adapted for use in a mechanically operated atomizer to produce an inhalable aerosol of a liquid medicament without the use of propellant gas.

SUMMARY

Some prior art aerosol dispensers are activated by opening the base and directly manually pushing a container into the aerosol dispenser such that a closure of the container is pierced by the conveying tube. Thereby, the conveying tube is brought into liquid communication with the container. One problem with this type of activation is that the user has to directly manually push the container quite far into the aerosol dispenser. A further problem with this type of activation is that the user has to directly manually push the container with a rather high force. This is particularly problematic for elderly and/or weak users. At least for these reasons, this type of activation of an aerosol dispenser has a reduced usability.

One object of the present disclosure is to provide an arrangement for activating an aerosol dispenser, which arrangement improves usability of the aerosol dispenser.

A further object of the present disclosure is to provide an arrangement for activating an aerosol dispenser, which arrangement enables activation of the aerosol dispenser with a loading rotation of the base, e.g. with the same type of rotation of the base as for loading a dose chamber with liquid prior to a shot with the aerosol dispenser. Thereby, a manual direct pushing of the container can be avoided.

A still further object of the present disclosure is to provide an inexpensive arrangement for activating an aerosol dispenser.

A still further object of the present disclosure is to provide an arrangement for activating an aerosol dispenser, which arrangement solves several or all of the foregoing objects.

A still further object of the present disclosure is to provide an aerosol dispenser comprising an arrangement, which aerosol dispenser solves one, several or all of the foregoing objects.

A still further object of the present disclosure is to provide a method for activating an aerosol dispenser, which method solves one, several or all of the foregoing objects.

According to one aspect, there is provided an arrangement for activating an aerosol dispenser, the arrangement comprising a conveying tube for conveying a liquid; a movable holding member holding the conveying tube; a rotatable base; and a container chamber between the holding member and the base; wherein the arrangement is configured to transmit a loading rotation of the base to a substantially axial loading movement, or an axial loading movement, of the holding member towards the base; and wherein the holding member comprises a locking structure exposed to the container chamber.

Throughout the present disclosure, the conveying tube may be configured to convey a liquid from a container to a dose chamber of the aerosol dispenser. Alternatively, or in addition, the base may be configured to support a bottom of the container in an inactivated state of the aerosol dispenser. In the inactivated state of the aerosol dispenser, there is no liquid communication between the container and the conveying tube. Thus, in the inactivated state, the liquid inside the container is free from bacteria. The inactivated state may alternatively be referred to as a storage position or inoperative position.

Throughout the present disclosure, the locking structure may be configured to attach the container to the holding member by means of the axial loading movement of the holding member, e.g. while the base supports the bottom of the container. The locking structure may for example be configured to attach to a mouth of the container. Throughout the present disclosure, the holding member may be referred to as a piston.

The base may be said to be positioned at a distal position of the aerosol dispenser. Thus, the axial loading movement may be a distal movement. A movement of the holding member in a direction opposite to the axial loading movement may be referred to as a delivery movement or release movement. The delivery movement may thus be a proximal movement, e.g. towards a spray nozzle unit of the aerosol dispenser.

When the base is rotated to make the loading rotation such that the holding member makes the axial loading movement, the locking structure may push the container against the base, which thereby functions as a support and provides a counterforce. The locking structure may be configured to attach the container to the holding member by means of a snap-fit. Thus, when the locking structure is pushed against the container with a certain force and the container is stopped by the base, the locking structure snaps onto the container.

In order to make the arrangement configured to transmit the loading rotation of the base to the axial loading movement of the holding member, the arrangement may for example comprise at least one cam profile and at least one cam follower for engaging the cam profile. The at least one cam profile may for example be fixed with respect to a stationary part (e.g. a housing of the aerosol dispenser) and the cam follower may be fixed with respect to the holding member, or vice versa. The at least one cam profile may be a helical surface. The helical surface may for example extend 140° to 175° around a longitudinal axis of the aerosol dispenser. However, the loading rotation of the base may be transmitted to the axial loading movement of the holding member in many alternative ways.

Throughout the present disclosure, the conveying tube may be configured to be brought into liquid communication with the container by means of the axial loading movement of the holding member. When the conveying tube is in liquid communication with the container, the aerosol dispenser adopts an activated state and the aerosol dispenser can be used for the first time. The activated state may alternatively be referred to as an operative position.

The conveying tube may be configured to pierce a closure of the container by means of the axial loading movement of the holding member. The closure may be provided over the mouth of the container. The closure may be constituted by a septum, for example a membrane. The piercing of the closure can be accomplished by the same loading rotation of the base as the loading rotation of the base during use of the aerosol dispenser. In this case, the locking structure may be configured to attach the container to the holding member substantially simultaneously, or simultaneously, as the conveying tube is brought into liquid communication with the container by means of the axial loading movement of the holding member.

The loading rotation of the base may for example be 180° for each aerosol shot. This loading rotation of the base may correspond to an axial loading movement of the holding member of 5-15 mm, such as 7-12 mm, such as 8-10 mm. Throughout the present disclosure, the base and the locking structure may be configured to hold the container therebetween when the aerosol dispenser is in the inactivated state.

The locking structure may comprise at least two resilient arms. The locking structure may for example comprise four, six or eight resilient arms, e.g. substantially evenly distributed, or evenly distributed, around the longitudinal axis of the aerosol dispenser. Each resilient arm may comprise a hook. Each hook may face inwardly, e.g. towards a longitudinal axis of the aerosol dispenser. As an alternative to resilient arms, the locking structure may be constituted by a resilient ring or other type of resilient structure.

The locking structure may be a protruding structure protruding into the container chamber. Alternatively, the locking structure may be constituted by an opening in the holding member for attachably receiving a mouth of the container, e.g. by means of a snap-fit.

The base may comprise a rigid structure protruding towards the holding member. The rigid structure may for example be constituted by a rigid collar protruding into the container chamber, i.e. in a proximal direction of the aerosol dispenser.

The base may comprise a resilient element facing the holding member. In this case, the arrangement may be configured such that the container can be stably held in the container chamber between the locking structure and the resilient element. The resilient element may therefore be said to provide an anti-rattling feature.

The resilient element may for example comprise, or be constituted by, foam rubber. In case the base comprises both a rigid structure and a resilient element, the rigid structure may be constituted by a rigid collar and the resilient element may be arranged at least partially inside the rigid collar. For example, the resilient element may have a generally cylindrical shape (at least in an uncompressed state) and be concentric with the rigid collar.

The resilient element may extend beyond the rigid structure towards the holding member in an uncompressed state of the resilient element. Throughout the present disclosure, the rigid structure may be arranged to limit compression of the resilient element by the container and to slightly compress/deform a stopper of the container to reduce the breakloose force.

When the base comprises a resilient element facing the holding member, the base may be rotated such that the resilient element is compressed by the bottom of the container due to the axial loading movement of the holding member, e.g. when the locking structure pushes the mouth of the container before the locking structure attaches to the container. As the base is rotated further and the axial loading movement of the holding member continues, a counterforce from the base on the bottom of the container will eventually become higher than the force required to attach the locking structure to the container, e.g. by means of a snap-fit. When this happens, further loading rotation of the base and further axial loading movement of the holding member will cause the locking structure to attach to the container. In other words, the resilient element may be compressed before the locking structure attaches to the container during loading rotation of the base.

The arrangement may be configured such that the counterforce from the base becomes higher than the force required to attach the locking structure to the container due to a certain opposing force from the resilient element or a contact between the bottom of the container and the rigid structure. Alternatively, or in addition, the arrangement and the container may be configured such that the counterforce from the base on the bottom of the container becomes higher than the force required to attach the locking structure to the container after a loading rotation of 70° to 110°, such as 85° to 95°, such as 90°, of the base from an initial position.

The arrangement may further comprise an elastic member configured to store mechanical energy from the axial loading movement of the holding member. The elastic member may for example be constituted by a coil spring. In this case, the container may be put inside the coil spring. The elastic member may be arranged in the container chamber.

The locking structure may project further towards the base than the conveying tube. Alternatively, or in addition, the locking structure may be substantially concentric with, or concentric with, the conveying tube.

According to a further aspect, there is provided a system comprising an arrangement according to the present disclosure and a container according to the present disclosure.

According to a further aspect, there is provided an aerosol dispenser comprising an arrangement according to the present disclosure. The aerosol dispenser may be a medical aerosol dispenser, i.e. for supplying a medical liquid. One example of an aerosol dispenser according to the present disclosure is an inhaler device. The base may be openable to expose the container chamber in order to put a container therein.

The aerosol dispenser may comprise a dose chamber. The volume of the dose chamber may be defined by the position of the conveying tube. The volume of the dose chamber may be expanded when the holding member (and the conveying tube attached thereto) makes the axial loading movement and may be compressed when the holding member (and the conveying tube attached thereto) makes the delivery movement.

The aerosol dispenser may further comprise a container. The container may be put in the container chamber during production of the aerosol dispenser. Alternatively, a user may open the base (by means of a rotation of the base opposite to the loading rotation), put the container in the container chamber (without having to push the container such that the conveying tube is brought into liquid communication with the container), and close the base. When the container is put in the container chamber and before the conveying tube is brought into liquid communication with the container, the aerosol dispenser is in an inactivated state.

Throughout the present disclosure, the container may be rigid. For example, the container may be made of glass, hard rigid plastic such as HDPE (high-density polyethylene) or a similar material. A bottom of the container may comprise a stopper according to the present disclosure. Alternatively, the container may comprise a rigid outer shell and a soft inner bag. In this case, the stopper can be omitted.

The container may be of a standard type, e.g. of a type used in injectors. The use of standard containers provides cost advantages. For example, already existing machinery may be used to fill the containers with a liquid, such as a drug. A container according to the present disclosure may be constituted by a cartridge.

The base and the locking structure may be configured to hold the container when the aerosol dispenser is in an inactivated state. Alternatively, or in addition, the locking structure may be configured to attach the container to the holding member by means of a snap-fit.

The conveying tube may be arranged to be brought into liquid communication with the container by means of the axial loading movement of the holding member, such that the aerosol dispenser adopts an activated state. The conveying tube may for example be arranged to pierce a closure over a mouth of the container by means of the axial loading movement of the holding member.

The locking structure may be configured to attach the container to the holding member by means of the axial loading movement of the holding member while the base supports a bottom of the container.

The locking structure may be arranged to attach the container to the holding member substantially simultaneously, or simultaneously, as the conveying tube is brought into liquid communication with the container by means of the axial loading movement of the holding member.

A bottom of the container may comprise a stopper arranged to be compressed by the rigid structure due to the axial loading movement of the holding member. In this way, the break-loose force of the stopper can be reduced. When the stopper has been compressed by the rigid structure, the stopper is slightly biased prior to expelling the first dose/priming dose from the dose chamber. After that, the stopper is only sucked into the container as the liquid therein decreases. Throughout the present disclosure, the stopper may be constituted by a plunger.

When the bottom of the container comprises a stopper arranged to be compressed by the rigid structure due to the axial loading movement of the holding member, the base may be rotated such that the locking structure attaches to the container due to the axial loading movement of the holding member. When the base is rotated further, the stopper may be compressed by the rigid structure due to the axial loading movement of the holding member. That is, the arrangement and the container may be configured such that the force required to compress the container by the rigid structure due to the axial loading movement of the holding member is higher than the force required for the locking structure to attach the container to the holding member by means of the axial loading movement of the holding member. In other words, the locking structure may attach to the container before the stopper is compressed by the rigid structure during the loading rotation of the base.

The arrangement and the container may be configured such that the stopper is compressed by the rigid structure after a loading rotation of 160° to 175°, such as 170°, of the base from an initial position. The stopper according to the present disclosure may be resilient. As the amount of liquid in the container decreases during use of the aerosol dispenser, the stopper moves towards the mouth of the container due to an underpressure in the container.

When the base comprises both the resilient element and the rigid structure and when the bottom of the container comprises a stopper arranged to be compressed by the rigid structure due to the axial loading movement of the holding member, the arrangement and the container may be configured such that loading rotation of the base and the consequential axial loading movement of the holding member first causes the resilient element to be compressed, then causes the locking structure to attach to the container (either due to a certain compression length of the resilient element or a contact between the bottom of the container and the rigid structure), and then causes the stopper to be compressed by the rigid structure.

According to a further aspect, there is provided a method for activating an aerosol dispenser, the method comprising providing a conveying tube for conveying a liquid from a container to a dose chamber of an aerosol dispenser; providing a rotatable base for supporting a bottom of the container in an inactivated state of the aerosol dispenser, in which inactivated state there is no liquid communication between the container and the conveying tube; providing a movable holding member holding the conveying tube, the holding member comprising a locking structure configured to attach the container to the holding member by means of a substantially axial loading movement, or axial loading movement, of the holding member towards the base while the base supports the bottom of the container; providing a container between the base and the holding member; rotating the base such that the holding member makes the axial loading movement, the locking structure attaches the container to the holding member, the conveying tube is brought into liquid communication with the container, and the aerosol dispenser thereby adopts an activated state.

BRIEF DESCRIPTION OF THE DRAWINGS

Further details, advantages and aspects of the present disclosure will become apparent from the following embodiments taken in conjunction with the drawings, wherein.

DETAILED DESCRIPTION

In the following, an arrangement for activating an aerosol dispenser, an aerosol dispenser comprising the arrangement and a method for activating an aerosol dispenser, will be described. The same reference numerals will be used to denote the same or similar structural features.

Figure 1:
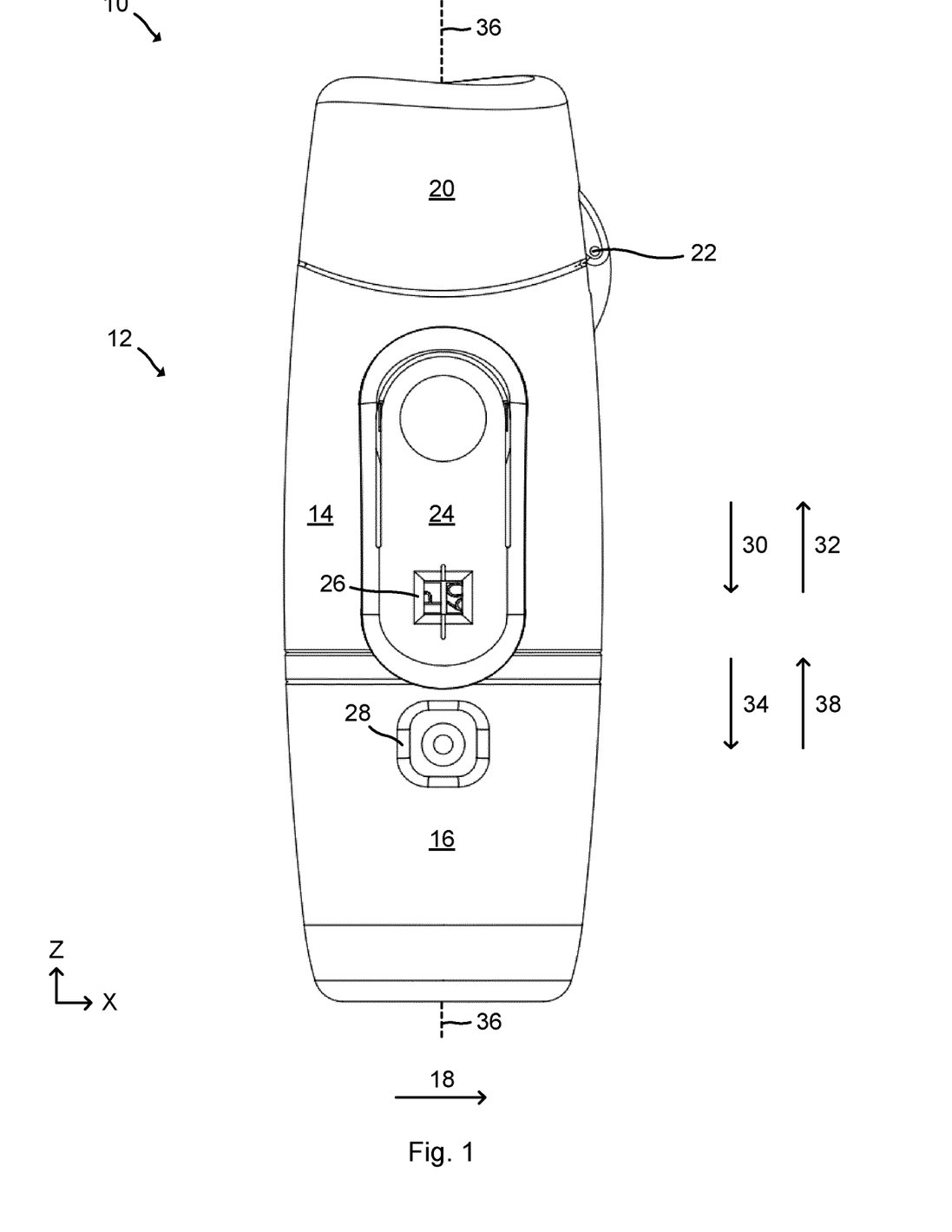
FIG. 1 represents a side view of an aerosol dispenser comprising an arrangement for activating the aerosol dispenser.

FIG. 1 represents a side view of an aerosol dispenser 10 comprising an arrangement 12 for activating the aerosol dispenser 10. The aerosol dispenser 10 comprises a housing 14 and a base 16 rotatable relative to the housing 14 to make a loading rotation 18. In FIG. 1, the base 16 is constituted by an exterior distal part (i.e. lower part in FIG. 1) of the aerosol dispenser 10.

The aerosol dispenser 10 in FIG. 1 further comprises an openable lid 20, connected to the housing 14 via a hinge 22, and a button 24 for triggering a dose shot. The aerosol dispenser 10 of this example further comprises a dose indicator 26 that indicates the number of doses left in the aerosol dispenser 10 and a state indicator window 28 for indicating whether the aerosol dispenser 10 is activated.

In FIG. 1, a holding member (not shown) and a needle or conveying tube (not shown) held by the holding member within the aerosol dispenser 10 are in an initial position. FIG. 1 further denotes an axial loading movement 30 and an axial release movement or delivery movement 32. The axial loading movement 30 is made in a distal direction 34 towards the base 16 along a longitudinal axis 36 of the aerosol dispenser 10. The delivery movement 32 is made in a proximal direction 38 towards the lid 20 along the longitudinal axis 36 of the aerosol dispenser 10. FIG. 1 further shows a Cartesian coordinate system for referencing purposes. The aerosol dispenser 10 may however be oriented arbitrarily in space.

Figure 2:
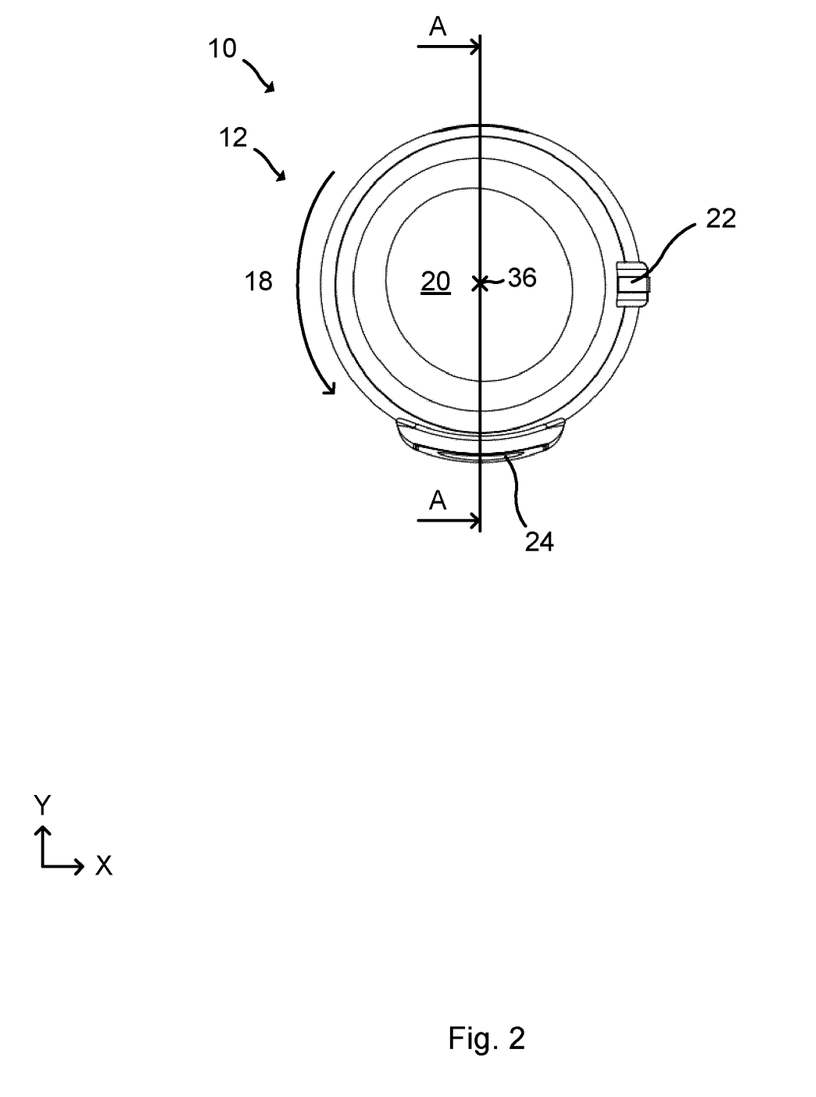
FIG. 2 represents a top view of the aerosol dispenser in FIG. 1.

FIG. 2 represents a top view of the aerosol dispenser 10. As can be seen in FIGS. 1 and 2, the aerosol dispenser 10 of this example has a generally cylindrical shape.

Figure 3:
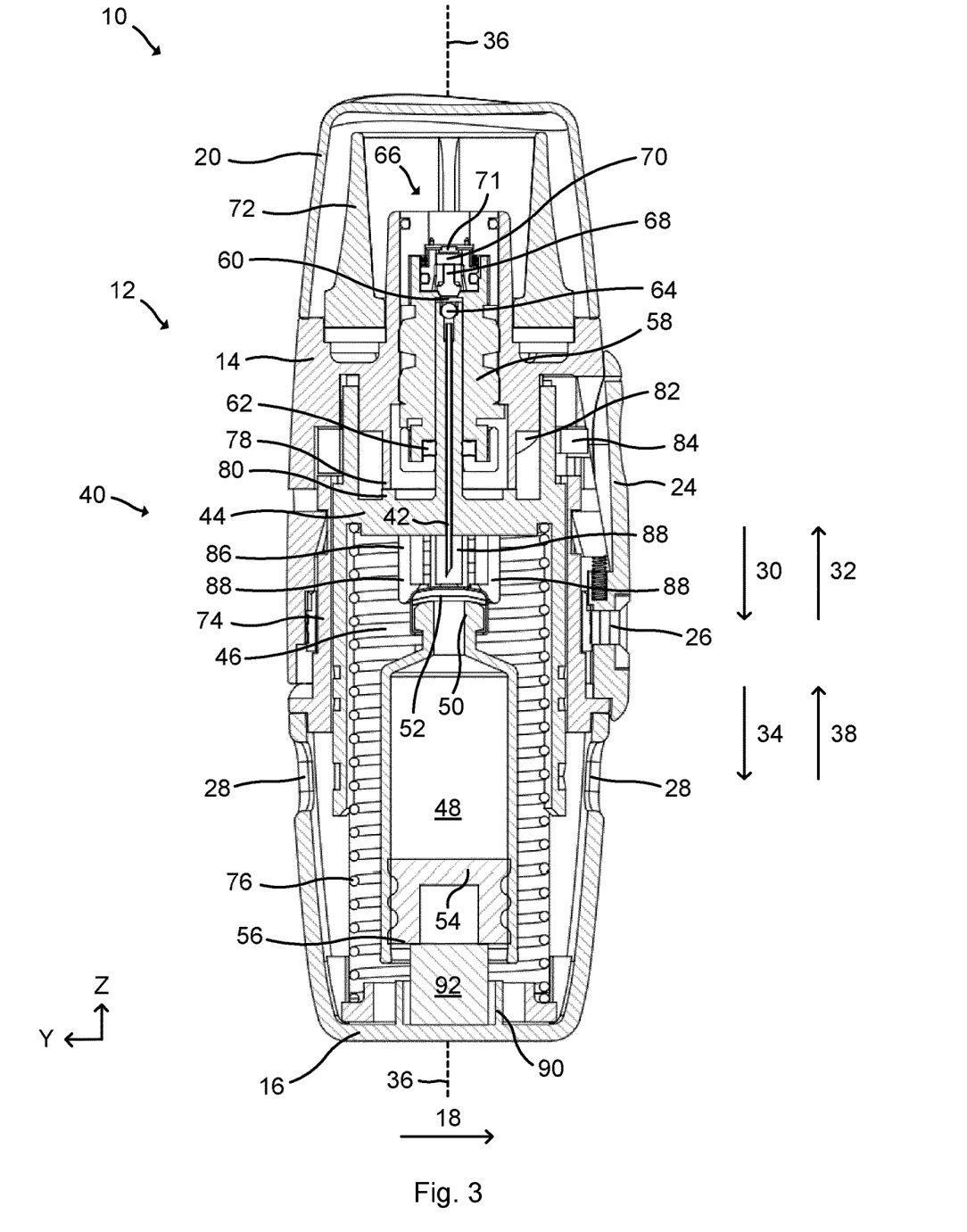
FIG. 3 represents a cross sectional side view of the aerosol dispenser along line A-A in FIG. 2 when the aerosol dispenser is in an inactivated state.

FIG. 3 represents a cross sectional side view of the aerosol dispenser 10 along line A-A in FIG. 2 when the aerosol dispenser 10 is in an inactivated state 40. In FIG. 3, the conveying tube 42 for conveying a liquid and the movable piston or holding member 44 can be seen. The holding member 44 firmly holds the conveying tube 42.

A container chamber 46 is provided between the holding member 44 and the base 16. As shown in FIG. 3, the container chamber 46 is provided between the holding member 44 and the base 16 along the longitudinal axis 36 of the aerosol dispenser 10. The aerosol dispenser 10 is loaded with a container 48 containing liquid, such as a drug, to be dispensed as an aerosol. The container 48 has been put into the container chamber 46 by opening the base 16.

The container 48 of the example in FIG. 3 comprises a neck or mouth 50 and a closure 52 provided over the mouth 50 to close the container 48. The container 48 in FIG. 3 further comprises a stopper 54 that closes a bottom 56 of the container 48. The container 48 in FIG. 3 is thereby hermetically closed. Thus, in the inactivated state 40 of the aerosol dispenser 10 in FIG. 3, there is no liquid communication between the container 48 and the conveying tube 42.

The container 48 can be produced independently of the arrangement 12. Alternatively, or in addition, the arrangement 12 may be produced independently of the remaining parts of the aerosol dispenser 10.

The aerosol dispenser 10 of this example further comprises a stationary pump cylinder 58, i.e. stationary with respect to the housing 14. A dose chamber 60 is provided in the pump cylinder 58. The conveying tube 42 is movable back and forth to expand and compress the volume of the dose chamber 60. A sealing 62, here exemplified as an X-ring, is provided to seal between the conveying tube 42 and the pump cylinder 58. The sealing 62 may alternatively be constituted by an O-ring, or by any other type of sealing known in the art.

The conveying tube 42 comprises an optional conveying tube check valve 64 at a proximal end of the conveying tube 42, i.e. at an opposite end with respect to the container 48. The conveying tube 42 is thereby in liquid communication with the dose chamber 60 via the conveying tube check valve 64.

The aerosol dispenser 10 further comprises a spray nozzle unit 66 having a spray nozzle 71 at a proximal side of the dose chamber 60. The spray nozzle unit 66 may for example comprise a spray nozzle check valve 68 and a membrane or filter 70. The aerosol dispenser 10 further comprises a mouthpiece 72 which is exposed to a user by opening the lid 20.

As can be seen in FIG. 3, the arrangement 12 of this example also comprises an optional inner sleeve 74. The inner sleeve 74 is fixedly connected to the base 16. The inner sleeve 74 and the holding member 44 are rotationally coupled. However, the holding member 44 is allowed to move axially relative to the inner sleeve 74 and the base 16. This type of coupling between the inner sleeve 74 and the holding member 44 may for example be realized by means of a pin engaged in a slot parallel with the longitudinal axis 36.

The arrangement 12 further comprises an elastic member 76, here constituted by a compression coil spring enclosing the container 48. The elastic member 76 is arranged in the container chamber 46 and contacts the base 16 and the holding member 44 in this example. The elastic member 76 is arranged to store mechanical energy from the axial loading movement 30 of the holding member 44 and the conveying tube 42 from the initial position in FIG. 3.

FIG. 3 further shows a housing stop 78 projecting distally from the housing 14 and a holding member stop 80 projecting proximally from the holding member 44. Expansion of the elastic member 76 is limited when the holding member stop 80 contacts the housing stop 78.

The arrangement 12 of this example comprises two cam profiles 82 (only one is visible in FIG. 3) and two cam followers (not visible in FIG. 3), each arranged to follow a respective cam profile 82. Each cam profile 82 of this example is a helical surface concentric with the longitudinal axis 36 of the aerosol dispenser 10. The arrangement 12 may alternatively comprise only one pair of a cam profile 82 and a cam follower, or more than two pairs. As a further alternative, the arrangement 12 may comprise only one cam profile 82 and two or more cam followers. As a further alternative, the tensioning arrangement 12 may comprise two or more cam profiles 82 and only one cam follower.

When the base 16 is manually rotated to make the loading rotation 18, the optional inner sleeve 74 rotates together with the base 16. The loading rotation 18 of the base 16 and the inner sleeve 74 is transmitted to a rotation of the holding member 44. The rotation of the holding member 44 causes the cam followers to travel along the associated cam profiles 82. Due to the cooperation between the cam followers and the cam profiles 82, the loading rotation 18 of the base 16 is transmitted to the axial loading movement 30 of the conveying tube 42 and the holding member 44 in the distal direction 34 against the force of the elastic member 76. This constitutes one of several examples for making the arrangement 12 transmit the loading rotation 18 of the base 16 to the axial loading movement 30 of the holding member 44 towards the base 16.

Furthermore, an actuator member 84 of the aerosol dispenser 10, here implemented as an actuator ring, can be seen in FIG. 3. The actuator member 84 is movable between a blocking position, in which the actuator member 84 blocks the holding member 44 and the conveying tube 42 from being released, and an unblocking position. In FIG. 3, the actuator member 84 is in the unblocking position.

The holding member 44 further comprises a locking structure 86 exposed to the container chamber 46. The locking structure 86 is configured to attach the container 48 to the holding member 44 by means of the axial loading movement 30 towards the base 16.

In the example in FIG. 3, the locking structure 86 is a protruding structure that protrudes in the distal direction 34 into the container chamber 46. The locking structure 86 projects from the holding member 44 in the distal direction 34.

As can be seen in FIG. 3, the locking structure 86 projects further towards the base 16 than the conveying tube 42. The locking structure 86 and the conveying tube 42 are in this example concentric with the longitudinal axis 36 of the aerosol dispenser 10. In FIG. 3, the locking structure 86 comprises a plurality of resilient arms 88 (four in FIG. 3, of which only three are visible). Each resilient arm 88 comprises a hook at its tip.

In the example in FIG. 3, the base 16 comprises a rigid structure 90 protruding towards the holding member 44, i.e. protruding in the proximal direction 38. The base 16 in FIG. 3 further comprises a resilient element 92 facing the holding member 44, i.e. facing in the proximal direction 38. The resilient element 92 extends beyond the rigid structure 90 in an uncompressed state of the resilient element 92.

When the container 48 is inserted into the container chamber 46 and the base 16 is closed, the top of the mouth 50 of the container 48 abuts against the tips of the resilient arms 88 and the bottom 56 of the container 48, in this case the stopper 54 of the container 48, is supported by the resilient element 92 of the base 16. In this state, the resilient element 92 is slightly compressed. The container 48 is thereby stably held within the container chamber 46 in the inactivated state 40 of the aerosol dispenser 10. As shown in FIG. 3, the container 48 is held in a position substantially concentric with, or concentric with, the longitudinal axis 36 of the aerosol dispenser 10.

Figure 4:
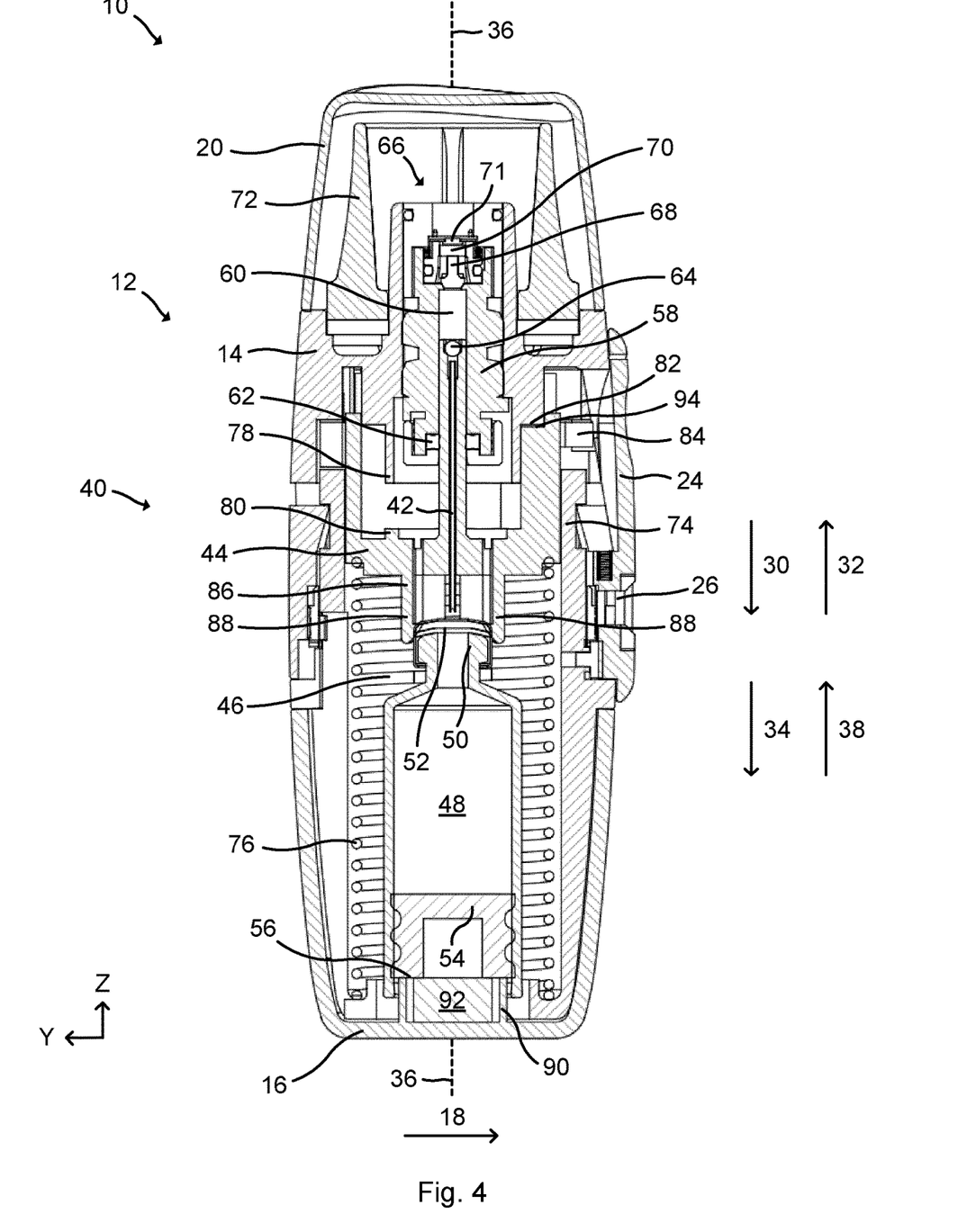
FIG. 4 represents a cross sectional side view of the aerosol dispenser in the inactivated state during an axial loading movement of a holding member.

FIG. 4 represents a cross sectional side view of the aerosol dispenser 10 in the inactivated state 40 during the axial loading movement 30 of the holding member 44 as the base 16 makes the loading rotation 18. In FIG. 4, the base 16 has rotated approximately 90° from the initial position in FIG. 3.

In FIG. 4, one of the two cam followers 94 engaging an associated cam profile 82 can be seen. The two cam followers 94 are fixed relative to the holding member 44. More specifically each cam follower 94 is integrally formed with the holding member 44 and projects in parallel with the longitudinal axis 36 towards the cam profile 82, i.e. in the proximal direction 38.

While the resilient arms 88 abut on top of the mouth 50 of the container 48, the axial loading movement 30 of the holding member 44 causes the bottom 56 of the container 48 to compress the resilient element 92.

The resilient element 92 is compressed until the bottom 56 of the container 48, in this case the stopper 54, abuts the rigid structure 90 of the base 16. Thus, the force required to compress the resilient element 92 is lower than the force required to snap the resilient arms 88 over the mouth 50 of the container 48.

Figure 5:
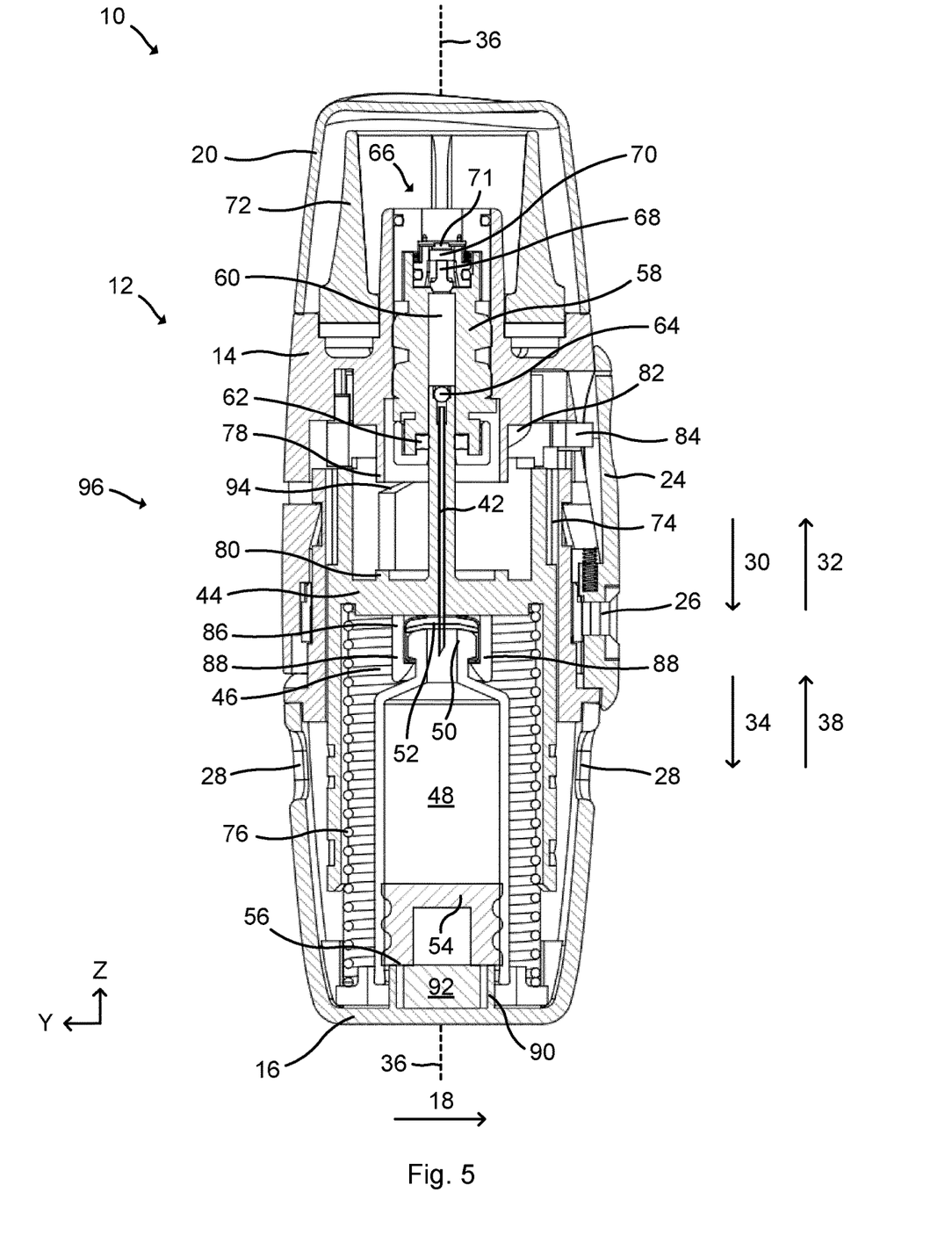
FIG. 5 represents a cross sectional side view of the aerosol dispenser in an activated state.

FIG. 5 represents a cross sectional side view of the aerosol dispenser 10 in an activated state 96. When the bottom 56 of the container 48 has been stopped by the base 16, further loading rotation 18 of the base 16 and consequential further axial loading movement 30 of the holding member 44 causes the locking structure 86 to be snap-fitted over the mouth 50 of the container 48. More specifically, the hooks of the resilient arms 88 snap over the mouth 50 of the container 48. The locking structure 86 thereby attaches the container 48 to the holding member 44 by means of the axial loading movement 30 towards the base 16 while the base 16 supports the bottom 56 of the container 48.

At the same time, or at substantially the same time, as the locking structure 86 attaches to the container 48, the axial loading movement 30 of the holding member 44 causes the conveying tube 42 to pierce the closure 52 of the container 48 to thereby be brought into liquid communication with the container 48. The aerosol dispenser 10 has thereby adopted the activated state 96. As soon as the closure 52 is pierced, the underpressure in the dose chamber 60 causes liquid to be sucked from the container 48 to the dose chamber 60.

When the base 16 is rotated further to continue the loading rotation 18, the container 48, which is now attached to the holding member 44, continues the axial loading movement 30 such that the rigid structure 90 compresses the stopper 54. The stopper 54 is thereby broken loose from the container 48 and is then ready to travel in the proximal direction 38 inside the container 48 by underpressure as the liquid in the container 48 is reduced. Silicone may optionally be provided on the stopper 54 to reduce friction.

In FIG. 5, the base 16 has rotated approximately 170° from the initial position in FIG. 3. Thus, the attachment of the locking structure 86 to the container 48 may take place at approximately 170°. The last 10° rotation of the base 16 of a 180° rotation may be used to compress the stopper 54 by the rigid structure 90.

The actuator member 84 can be moved from the unblocking position to the blocking position by means of the loading rotation 18 of the base 16. The holding member 44 and the conveying tube 42 are then held in a tensioning position by means of the actuator member 84. When the conveying tube 42 is in the tensioning position, the volume of the dose chamber 60 corresponds to one dose.

The button 24 is operatively coupled to the actuator member 84. By pushing the button 24, the actuator member 84 can be moved from the blocking position to the unblocking position such that the actuator member 84 no longer blocks the holding member 44. As a consequence, the entire force from the elastic member 76 acts on the liquid in the dose chamber 60 via the holding member 44, the conveying tube 42 and the conveying tube check valve 64. The force in the elastic member 76 may for example be 5-50 N. The high pressure in the dose chamber 60 presses the liquid through the spray nozzle check valve 68 and the filter 70 of the spray nozzle unit 66. The liquid is thereby expelled as an aerosol as a first dose or priming dose. The pressure in the dose chamber 60 may be approximately 15-75 bar. This enables the use of a relatively small spring as elastic member 76.

When the holding member 44 has returned to the initial position according to FIG. 3 and the container 48 is attached to the locking structure 86, a mark on the container 48 may be visible through the state indicator window 28. This confirms that the aerosol dispenser 10 has adopted the activated state 96. In order to expel a further dose (or a first dose in case a priming dose was expelled first), the base 16 may be rotated again to make the loading rotation 18 such that the conveying tube 42 makes the axial loading movement 30, the volume of the dose chamber 60 expands and an underpressure is established in the dose chamber 60. Consequently, liquid in the container 48 is again sucked by the conveying tube 42 into the dose chamber 60. An underpressure is thereby generated in the container 48 which causes the stopper 54 to travel in the proximal direction 38. The further dose (or a first dose in case a priming dose was expelled first) may then be expelled by pushing the button 24.

While the present disclosure has been described with reference to exemplary embodiments, it will be appreciated that the present disclosure is not limited to what has been described above. For example, it will be appreciated that the dimensions of the parts may be varied as needed.

The invention claimed is:

1. An arrangement for activating an aerosol dispenser, the arrangement comprising:

- a conveying tube for conveying a liquid;
- a movable holding member holding the conveying tube;
- a rotatable base; and
- a container chamber between the holding member and the base;
- wherein the arrangement is configured to transmit a loading rotation of the base to an axial loading movement of the holding member towards the base;
- wherein the holding member comprises a locking structure exposed to the container chamber; and
- wherein the locking structure projects further towards the base than the conveying tube.

2. The arrangement according to claim 1, wherein the locking structure comprises at least two resilient arms.

3. The arrangement according to claim 1, wherein the base comprises a rigid structure protruding towards the holding member.

4. The arrangement according to claim 3, wherein a resilient element extends beyond the rigid structure towards the holding member in an uncompressed state of the resilient element.

5. The arrangement according to claim 1, wherein the base comprises a resilient element facing the holding member.

6. An aerosol dispenser comprising the arrangement according to claim 1.

7. The aerosol dispenser according to claim 6, further comprising a container.

8. The aerosol dispenser according to claim 7, wherein the base and the locking structure are configured to hold the container when the aerosol dispenser is in an inactivated state.

9. The aerosol dispenser according to claim 7, wherein the locking structure is configured to attach the container to the holding member by means of a snap-fit.

10. The aerosol dispenser according to claim 7, wherein the conveying tube is arranged to be brought into liquid communication with the container by means of the axial loading movement of the holding member, such that the aerosol dispenser adopts an activated state.

11. The aerosol dispenser according to claim 10, wherein the locking structure is arranged to attach the container to the holding member simultaneously as the conveying tube is brought into liquid communication with the container by means of the axial loading movement of the holding member.

12. The aerosol dispenser according to claim 7, wherein the locking structure is configured to attach the container to the holding member by means of the axial loading movement of the holding member while the base supports a bottom of the container.

13. The aerosol dispenser according to claim 7, wherein a bottom of the container comprises a stopper arranged to be compressed by the rigid structure due to the axial loading movement of the holding member.

14. A method for activating an aerosol dispenser, the method comprising:

- providing a conveying tube for conveying a liquid from a container to a dose chamber of the aerosol dispenser;
- providing a rotatable base for supporting a bottom of the container in an inactivated state of the aerosol dispenser, in which inactivated state there is no liquid communication between the container and the conveying tube;
- providing a movable holding member holding the conveying tube, the holding member comprising a locking structure configured to attach the container to the holding member by means of an axial loading movement of the holding member towards the base while the base supports the bottom of the container;
- providing a container between the base and the holding member;
- rotating the base such that the holding member makes the axial loading movement, the locking structure attaches the container to the holding member, the conveying tube is brought into liquid communication with the container, and the aerosol dispenser thereby adopts an activated state.

* * * * *